United States Patent [19]

Lang et al.

[11] Patent Number: 5,516,805
[45] Date of Patent: May 14, 1996

[54] 3,5-SUBSTITUTED AMINOBENZOYLGUANIDINES, THEIR USE AS A MEDICAMENT OR DIAGNOSTIC AND MEDICAMENT CONTAINING THEM

[75] Inventors: Hans-Jochen Lang; Heinrich Englert, both of Hofheim/Ts; Andreas Weichert, Frankfurt am Main; Heinz-Werner Kleemann, Bad Homburg; Wolfgang Scholz, Eschborn; Udo Albus, Florstadt, all of Germany

[73] Assignee: Hoechst Aktiengesellschaft, Frankfurt am Main, Germany

[21] Appl. No.: 450,225

[22] Filed: May 25, 1995

Related U.S. Application Data

[63] Continuation of Ser. No. 351,570, Dec. 7, 1994, abandoned, which is a continuation of Ser. No. 165,952, Dec. 14, 1993, abandoned.

[30] Foreign Application Priority Data

Dec. 16, 1992 [DE] Germany .................. 42 42 554.9

[51] Int. Cl.$^6$ .................. C07C 311/16; A61K 31/165
[52] U.S. Cl. .................. 514/620; 564/164; 564/165
[58] Field of Search .................. 564/164, 165; 514/620

[56] References Cited

U.S. PATENT DOCUMENTS 3,780,027 12/1973 Cragoe, Jr. et al. .................. 564/85
5,091,394 2/1992 Englert et al. .................. 514/331

FOREIGN PATENT DOCUMENTS 242470 2/1961 Australia .................. 564/86
0416499A3 3/1991 European Pat. Off. .
2246352 1/1992 United Kingdom .................. 564/164

OTHER PUBLICATIONS

M. S. Glitzer et al., "N–Amidino–3–Amino–6–Chloropyrazinecarboxamide: A New Diuretic Which Antagonizes the Renal Actions of Aldosterone", Proceedings of the Society for Experimental Biology and Medicine, 120:364–367 (1965).

P. Mildner et al., Inhibition of Urease by some Triazole, Urea, and Guanidine Derivatives, Chemical Abstracts, 81(23):168, 147547g (1974).

Primary Examiner—Jacqueline Haley
Attorney, Agent, or Firm—Finnegan, Henderson, Farabow, Garrett & Dunner

[57] ABSTRACT

3,5-Substituted aminobenzoylguanidines, process for their preparation, their use as a medicament or diagnostic and medicament containing them There are described benzoylguanidines of the formula I

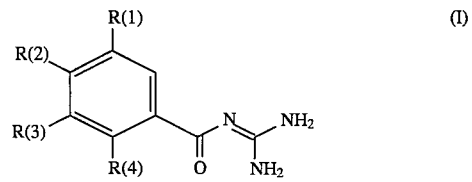

where one of the substituents R(1), R(2), R(3) or R(4) is: an amino group

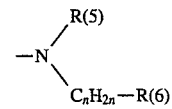

where R(5), R(6)=inter alia, H or alkyl, or alternatively R(5) and R(6), together with the nitrogen atom, are a 5-7-membered ring, and the other substituents R(1), R(2), R(3) and R(4) in each case are: H, Hal, CN, CF$_3$, NO$_2$, CF$_3$—O—, C$_m$F$_{2m+1}$—CH$_2$—O—, R(11)—C$_q$H$_{2q}$—X$_p$—, X=O or NR(12), R(11)=H, (cyclo)alkyl, phenyl, and where R(1) and R(4) are not simultaneously hydrogen.

The compounds I have very good antiarrhythmic and cardioprotective properties, but no undesired salidiuretic properties. They additionally exhibit protective properties against is chemically induced damage in vivo and in vitro in different organs and gastroprotective properties as a result of inhibition of gastric acid secretion. Moreover, they are distinguished by inhibitory action on the proliferation of cells.

19 Claims, No Drawings

3,5-SUBSTITUTED AMINOBENZOYLGUANIDINES, THEIR USE AS A MEDICAMENT OR DIAGNOSTIC AND MEDICAMENT CONTAINING THEM

This application is a continuation of prior application Ser. No. 08/351,570 filed Dec. 7, 1994, now abandoned which is a continuation of application Ser. No. 08/165,952 filed Dec. 14, 1993, now abandoned.

The invention relates to benzoylguanidines of the formula I

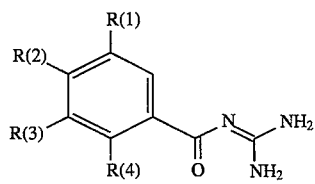

in which: one of the substituents R(1), R(2), R(3) or R(4) is: an amino group

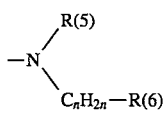

where R(5)=hydrogen or $C_{(1-6)}$-alkyl, n=zero, 1, 2, 3 or 4, R(6)=H, $C_{(1-4)}$-alkyl, in which a $CH_2$ group can be replaced by 1 sulfur atom or a group NR(7) where R(7)=hydrogen, methyl or ethyl, $C_{(3-8)}$-cycloalkyl, phenyl, which is unsubstituted or carries 1, 2 or 3 substituents from the group comprising F, Cl, Br, methyl, methoxy and —NR(8)R(9) where R(8) and R(9) are H, methyl or ethyl, and in which R(5) and R(6), together with the nitrogen atom, can also form a 5-, 6- or 7-membered ring in which 1 carbon atom can be replaced by oxygen, S or NR(10) in the sense of morpholino, thiomorpholino and piperazino where R(10) is H, $C_{(1-3)}$-alkyl or benzyl, and the other substituents R(1), R(2), R(3) and R(4) in each case are:

hydrogen, F, Cl, Br, I, CN, $CF_3$, $NO_2$, $CF_3$—O—, $C_mF_{2m+1}$—$CH_2$—O— where m=1, 2 or 3, R(11)—$C_qH_{2q}$—$X_p$— where q=zero, 1, 2, 3 or 4, p=zero or 1,

X=oxygen or NR(12), R(12)=H or $C_{(1-3)}$-alkyl,

R(11)=hydrogen, $C_{(1-6)}$-alkyl, $C_{(3-8)}$-cycloalkyl, phenyl which is unsubstituted or substituted by 1, 2 or 3 substituents from the group comprising F, Cl, $CH_3$, $CH_3$—O—, NR(13)R(14) where R(13), R(14) is H, methyl or ethyl and where R(1) and R(4) are not simultaneously hydrogen.

Preferred compounds of the formula I are those in which: one of the substituents R(1), R(2), R(3) or R(4) is: an amino group

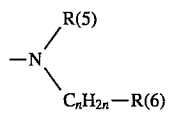

where R(5)=hydrogen or $C_{(1-4)}$-alkyl, n=zero, 1 or 2, and R(6)=H, $C_{(1-4)}$-alkyl, in which a $CH_2$ group can be replaced by a sulfur atom or a group NR(7) where R(7)=H, methyl or ethyl, $C_{(3-6)}$-cycloalkyl, phenyl, which is unsubstituted or carries 1, 2 or 3 substituents from the group comprising F, Cl, Br, methyl, methoxy and —NR(8)R(9) where R(8) and R(9) are H, methyl, ethyl, and in which R(5) and R(6), together with the nitrogen atom, can also form a 5-, 6- or 7-membered ring, and the other substituents R(1), R(2), R(3) and R(4) in each case are:

hydrogen, F, Cl, Br, I, $CF_3$, $NO_2$, $C_mF_{2m+1}$—$CH_2$—O— where m=1, 2 or 3, R(11)—$C_qH_{2q}$—$X_p$— where q=zero, 1 or 2, p32 zero or 1, X=oxygen R(11)=hydrogen, $C_{(1-6)}$-alkyl, $C_{(5-6)}$-cycloalkyl, phenyl which is unsubstituted or is substituted by 1 or 2 substituents from the group comprising F, Cl, methyl and $CH_3$—O—, and where R(1) and R(4) are not simultaneously hydrogen.

Particularly preferred compounds of the formula I are those in which:

R(4) is hydrogen, one of the substituents R(1), R(2) or R(3) is: an amino group

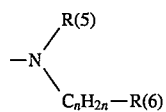

where R(5)=hydrogen or $C_{(1-4)}$-alkyl, n=zero, 1 or 2, and R(6)=H, $C_{(1-4)}$-alkyl, $C_{(5-6)}$-cycloalkyl, phenyl, which is unsubstituted or carries 1 or 2 substituents from the group comprising F, Cl and methyl and the other substituents R(1), R(2) and R(3) in each case are:

hydrogen, F, Cl, $CF_3$, R(11)—$C_q$—$H_{2q}$—$X_p$— where q=zero to 2, p=zero or 1, X=oxygen, R(11)=hydrogen, $C_{(1-4)}$-alkyl, $C_{(5-6)}$-cycloalkyl, phenyl which is unsubstituted or substituted by 1 or 2 substituents from the group comprising F, Cl, methyl and $CH_3$—O—, and where R(1) and R(4) are not hydrogen.

Very particularly preferred compounds are 2-amino- 3,5-dichlorobenzoylguanidine hydrochloride, 5-trifluoromethyl-3-N, N-dimethylaminobenzoylguanidine hydrochloride, 4-amino-3,5-dibromobenzoylguanidine hydrochloride and their pharmacologically tolerable salts.

If one of the substituents R(1) to R(4) contains a center of asymmetry, the invention includes compounds having either the S or R configuration. The compounds can be present as optical isomers, as diastereomers, as racemates or as mixtures thereof.

The designated alkyl radicals can be present either in straight-chain or branched form.

The invention furthermore relates to a process for the preparation of a compound I, which comprises reacting a compound of the formula II

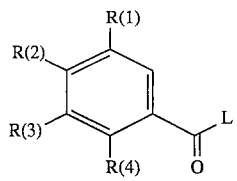

in which R(1) to R(4) have the given meaning and L is a leaving group which can be easily nucleophilically substituted, with guanidine.

The activated acid derivatives of the formula II in which L is an alkoxy group, preferably a methoxy group, a phenoxy group, a phenylthio, methylthio or 2-pyridylthio group, or a nitrogen heterocycle, preferably 1-imidazolyl, are advantageously obtained in a manner known per se from the carbonyl chlorides (formula II, L=Cl) on which they are based, which for their part can in turn be prepared in a manner known per se from the carboxylic acids (formula II, L=OH) on which they are based, for example using thionyl chloride.

In addition to the carbonyl chlorides of the formula II (L=Cl), other activated acid derivatives of the formula II can also be prepared in a manner known per se directly from the benzoic acid derivatives (formula II, L=OH) on which they are based, such as, for example, the methyl esters of the formula II where L=OCH$_3$, by treatment with gaseous HCl in methanol, the imidazolides of the formula II by treatment with carbonyldiimidazole [L=1-imidazolyl, Staab, Angew. Chem. Int. Ed. Engl. 1, 351–367 (1962)], the mixed anhydrides II using Cl—COOC$_2$H$_5$ or tosyl chloride in the presence of triethylamine in an inert solvent, and also the activation of benzoic acids using dicyclohexylcarbodiimide (DCC) or using O-[(cyano(ethoxycarbonyl)methylene)amino]-1,1,3,3-tetramethyl-uronium tetrafluoborate ("TOTU") (Proceedings of the 21st European Peptide Symposium, Peptides 1990, Editors E. Giralt and D. Andreu, Escom, Leiden, 1991). A number of suitable methods for the preparation of activated carboxylic acid derivatives of the formula II are given under details of source literature in J. March, Advanced Organic Chemistry, Third Edition (John Wiley & Sons, 1985), p. 350.

The reaction of an activated carboxylic acid derivative of the formula II with guanidine is carried out in a manner known per se in a protic or aprotic polar but inert organic solvent. Methanol or THF between 20° C. and the boiling point of these solvents have proven suitable in the reaction of the methyl benzoates (II, L=OMe) with guanidine. In most reactions of compounds II with salt-free guanidine, the reaction was advantageously carried out in aprotic inert solvents such as THF, dimethoxyethane or dioxane. However, water can also be used as a solvent in the reaction of II and III if a base such as, for example, NaOH is used.

If L=Cl, the reaction is advantageously carried out with the addition of an acid scavenger, for example in the form of excess guanidine for binding the hydrohalic acid.

Some of the underlying benzoic acid derivatives of the formula II are known and described in the literature. The unknown compounds of the formula II can be prepared by methods known from the literature.

Carboxylic acids or their esters of the formula II (e.g. L=—OH or —O—methyl) where R(2) is halogen or R(3) is nitro can be used as versatile starting compounds for further carboxylic acids of the formula II, where the halogen in position R(2) can very conveniently be replaced in a known manner by numerous nucleophilic reagents, such as mercaptans R(10)—SH, phenols R(10)—OH or primary or secondary amines

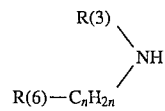

with the formation of other benzoic acid derivatives II where L=—OH or —O—methyl, or nitro can be converted into NH$_2$ by reductive transformation in numerous reactions (alkylations, acylations, diazotizations with subsequent Sandmeyer, Ullmann or Meerwein reactions etc.) in other benzoic acid derivatives II where L=—OH or —O—methyl.

In general, benzoylguanidines I are weak bases and can bind acid with the formation of salts. Possible acid addition salts are salts of all pharmacologically tolerable acids, for example halides, in particular hydrochlorides, lactates, sulfates, citrates, tartrates, acetates, phosphates, methanesulfonates and p-toluene-sulfonates.

The compounds I are substituted acylguanidines. The most prominent representative of the acylguanidines is the pyrazine derivative amiloride, which is used in therapy as a potassium-sparing diuretic. Numerous other compounds of the amiloride type are described in the literature, such as, for example, dimethylamiloride or ethylisopropylamiloride.

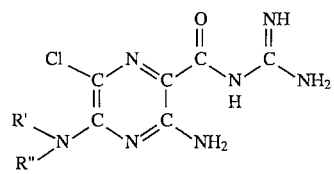

Amiloride: R', R"=H
Dimethylamiloride: R', R"=CH$_3$
Ethylisopropylamiloride: R'=C$_2$H$_5$, R"=CH(CH$_3$)$_2$ Investigations have moreover been disclosed which point to antiarrhythmic properties of amiloride [Circulation 79, 1257–63 (1989)]. Obstacles to wide use as an antiarrhythmic are, however, that this effect is only slightly pronounced and occurs accompanied by a hypotensive and saluretic action and these side effects are undesired in the treatment of cardiac arrhythmias.

Indications of antiarrhythmic properties of amiloride were also obtained in experiments on isolated animal hearts [Eur. Heart J. 9 (suppl.1): 167 (1988)] (book of abstracts). For instance, it was found in rat hearts that an artificially induced ventricular fibrillation could be suppressed completely by amiloride. The abovementioned amiloride derivative ethylisopropylamiloride was even more potent than amiloride in this model.

U.S. Pat. No. 5,09 1,394 describes benzoylguanidines which carry a hydrogen atom in the position corresponding to the radical R(1) and R(4).

Other benzoylguanidines are mentioned in the literature reference Kumamoto Pharm. Bull. [1966], pp. 7–13.

In U.S. Pat. No. 3,780,027, acylguanidines are claimed which are structurally similar to the compounds of the formula I and are derived from commercially available loop diuretics, such as bumetanide. A strong salidiuretic activity is correspondingly reported for these compounds.

It was therefore surprising that the compounds according to the invention have no undesired and disadvantageous salidiuretic properties, but very good antiarrhythmic properties, as occur, for example, in the case of oxygen deficiency symptoms. As a result of their pharmacological properties, the compounds are outstandingly suitable as antiarrhythmic pharmaceuticals having a cardioprotective component for infarct prophylaxis and infarct treatment and for the treatment of angina pectoris, where they also preventively inhibit or greatly decrease the pathophysiological processes in the formation of is chemically induced damage, in particular in the production of is chemically induced cardiac arrhythmias. Because of their protective actions against pathological hypoxic and ischemic situations, the compounds of the formula I according to the invention can be used as a result of inhibition of the cellular $Na^+/H^+$ exchange mechanism as pharmaceuticals for the treatment of all acute or chronic damage caused by ischemia or primary or secondary diseases induced thereby. This relates to their use as pharmaceuticals for surgical interventions, for example in organ transplantation, where the compounds can be used both for the protection of the organs in the donor before and during removal, for the protection of removed organs, for example during treatment with or storage thereof in physiological bath fluids, and during transfer to the body of the recipient. The compounds are likewise useful protective pharmaceuticals during the performance of angioplastic surgical interventions, for example on the heart and on peripheral vessels. In accordance with their protective action against is chemically induced damage, the compounds are also suitable as pharmaceuticals for the treatment of ischemias of the nervous system, in particular the CNS, where they are suitable, for example, for the treatment of a stroke or of cerebral edema. Moreover the compounds of the formula I according to the invention are also suitable for the treatment of forms of shock, such as, for example, allergic, cardiogenic, hypovolemic and bacterial shock.

Moreover, the compounds of the formula I according to the invention are distinguished by potent inhibitory action on the proliferation of cells, for example fibroblast cell proliferation and the proliferation of vascular smooth muscle cells. The compounds of the formula I can therefore be considered as useful therapeutics for diseases in which cell proliferation is a primary or secondary cause, and can therefore be used as antiatherosclerotics, agents against diabetic late complications, cancers, fibrotic diseases such as pulmonary fibrosis, fibrosis of the liver or fibrosis of the kidneys, organ hypertrophies and hyperplasias, in particular in prostate hyperplasia or prostate hypertrophy. The compounds I additionally show gastroprotective properties as a result of inhibition of gastric secretion.

The compounds according to the invention are effective inhibitors of the cellular sodium-proton antiporter ($Na^+/H^+$ exchanger), which is raised in numerous diseases (essential hypertension, atherosclerosis, diabetes, etc.) even in those cells which are easily accessible to measurements, such as, for example, in erythrocytes, platelets or leucocytes. The compounds according to the invention are therefore suitable as outstanding and simple scientific tools, for example in their use as diagnostics for the determination and differentiation of certain forms of hypertension, but also of atherosclerosis, diabetes, proliferative diseases etc.

Moreover, the compounds of the formula I are suitable for preventive therapy for the prevention of the formation of high blood pressure, for example of essential hypertension.

Pharmaceuticals which contain a compound I can be administered orally, parenterally, intravenously, rectally or by inhalation, the preferred administration being dependent on the particular type of the disease. The compounds I can be used on their own or together with pharmaceutical auxiliaries, to be precise both in veterinary and in human medicine.

The auxiliaries which are suitable for the desired pharmaceutical formulation are familiar to the person skilled in the art on the basis of his expert knowledge. In addition to solvents, gelling agents, suppository bases, tabletting auxiliaries and other active compound excipients, antioxidants, dispersants, emulsifiers, antifoams, flavor correctants, preservatives, solubilizers or colorants, for example, can be used.

For a form for oral administration, the active compounds are mixed with the additives suitable for this purpose, such as excipients, stabilizers or inert diluents, and are brought by the customary methods into the suitable administration forms, such as tablets, coated tablets, hard gelatine capsules, or aqueous, alcoholic or oily solutions. Inert excipients which can be used are, for example, gum arabic, magnesia, magnesium carbonate, potassium phosphate, lactose, glucose or starch, in particular cornstarch. Preparation can be carried out here both as dry and as moist granules. Suitable oily excipients or solvents are, for example, vegetable or animal oils, such as sunflower oil or fish liver oil.

For subcutaneous or intravenous administration, the active compounds are brought into solution, suspension or emulsion, if desired using the substances customary for this purpose such as solubilizers, emulsifiers or other auxiliaries. Suitable solvents are, for example: water, physiological saline solution or alcohols, for example ethanol, propanol, glycerol, and also sugar solutions such as glucose or mannitol solutions, or alternatively a mixture of the various solvents mentioned.

Pharmaceutical formulations suitable for administration in the form of aerosols or sprays are, for example, solutions, suspensions or emulsions of the active compound of the formula I in a pharmaceutically acceptable solvent, such as, in particular, ethanol or water, or a mixture of such solvents.

If required, the formulation can also contain still other pharmaceutical auxiliaries such as surfactants, emulsifiers and stabilizers as well as a propellant gas. Such a preparation contains the active compound customarily in a concentration from about 0.1 to 10, in particular from about 0.3 to 3,% by weight.

The dose of the active compound of the formula I to be administered and the frequency of administration depend on the potency and duration of action of the compounds used and additionally on the type and severity of the disease to be treated and on the sex, age, weight and individual responsiveness of the mammal to be treated. On average, the daily dose of a compound of the formula I in a patient of weight about 75 kg is at least 0,001 mg/kg, preferably 0.01 mg/kg to 10 mg/kg, preferably 1 mg/kg of body weight. In acute episodes of the disease, for example immediately after suffering a cardiac infarct, even higher and in particular more frequent doses may be necessary, for example up to 4 individual doses per day. In particular when administered i.v., for example in the case of an infarct patient in the intensive care unit, up to 200 mg per day may be necessary.

EXPERIMENTAL SECTION

General procedure for the preparation of benzoylguanidines (I) from benzoic acids (II, L=OH)

0.01 mol of the benzoic acid derivative of the formula II is dissolved or suspended in 60 ml of anhydrous THF and then treated with 1.78 g (0.011 mol) of carbonyldiimidazole. After stirring for 2 hours at room temperature, 2.95 g (0.05 mol) of guanidine are introduced into the reaction solution. After stirring overnight, the THF is distilled off under reduced pressure (Rotavapor), the residue is treated with water, the mixture is adjusted to pH 6–7 with 2N HCL and the corresponding benzoylguanidine (formula I) is filtered

EXAMPLE 1

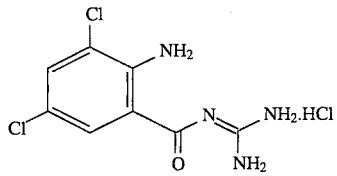

2-Amino-3,5-dichlorobenzoylguanidine hydrochloride is obtained according to the general procedure from 2-amino-3,5-dichlorobenzoic acid; colorless crystalline substance; m.p. 190° C. (dec.).

EXAMPLE 2

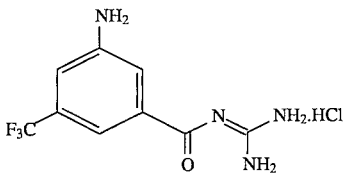

3-Amino-5-trifluoromethylbenzoylguanidine hydrochloride is obtained according to the general procedure from 3-amino-5-trifluoromethylbenzoic acid. Colorless crystalline substance: m.p. 225° C.

EXAMPLE 3

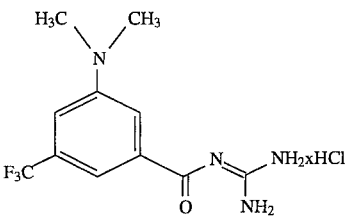

5-Trifluoromethyl-3-N,N-dimethylaminobenzoylguanidine hydrochloride is obtained according to the general procedure from 5-trifluoromethyl-3-N,N-dimethylaminobenzoic acid; colorless crystalline substance; m.p. 277° C.

5-Trifluoromethyl-3-N,N-dimethylaminobenzoic acid (m.p. 194°–197° C.) was obtained by reaction of 3-amino-5-trifluoromethylbenzoic acid with 3 times the equivalent amount of methyl iodide in DMF in the presence of finely ground anhydrous potassium carbonate at 60° C. for several hours and subsequent hydrolysis of the methyl 5-trifluoromethyl- 3-N,N-dimethylaminobenzoate thus obtained (m.p. 55°–60° C.) with aqueous-methanolic sodium hydroxide solution and subsequently rendering acidic with 2N HCl to pH 1–2.

EXAMPLE 4

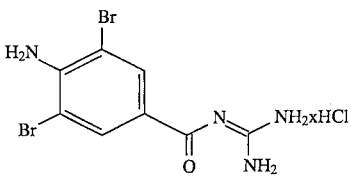

4-Amino-3,5-dibromobenzoylguanidine hydrochloride is obtained according to the general procedure from 4-amino-3,5-dibromobenzoic acid. Crystalline substance; m.p. 266°–269° C.

EXAMPLE 5

4-Amino-3,5-dimethylbenzoylguanidine dihydrochloride is obtained according to the general procedure from 4-amino-3,5-dimethylbenzoic acid. Crystalline substance; m.p.>330° C.

EXAMPLE 6

3-Bromo-5-methylbenzoylguanidine hydrochloride is obtained according to the general procedure from 3-bromo-5-methylbenzoic acid. Crystalline substance; m.p.>300° C.

EXAMPLE 7

3,5-Dibromo-4-(1-butylamino)benzoylguanidine dihydrochloride is obtained according to the general procedure from 3,5-dibromo-4-(1-butylamino)benzoic acid. Crystalline substance; m.p. 214°–215° C.

EXAMPLE 8

3-Amino-5-chlorobenzoylguanidine dihydrochloride is obtained according to the general procedure from 3-amino-5-chlorobenzoic acid. Crystalline substance; m.p. 270° C.

EXAMPLE 9

3-N,N-Dimethylamino-5-chlorobenzoylguanidine dihydrochloride is obtained according to the general procedure from 3-N,N-dimethylamino-5-chlorobenzoic acid. Crystalline substance; m.p. 217° C.

EXAMPLE 10

3,5-Dimethyl-4-N,N-dimethylamino-5-chlorobenzoylguanidine dihydrochloride is obtained according to the general procedure from 3,5-dimethyl-4-N,N-dimethylamino-5-chlorobenzoic acid. Crystalline substance; m.p. 203° C.

Example 11

2-Amino-4,5-dimethoxybenzoylguanidine dihydrochloride is obtained according to the general procedure from 2-amino-4,5-dimethoxybenzoic acid. Crystalline substance; m.p. 177° C.

EXAMPLE 12

2-Amino-4,5-dibromobenzoylguanidine dihydrochloride is obtained according to the general procedure from 2-amino-4,5-dibromobenzoic acid. Crystalline substance; m.p.>310° C.

EXAMPLE 13

5-Chloro-3-(4-chlorobenzylamino)benzoylguanidine dihydrochloride is obtained according to the general procedure from 5-chloro-3-(4-chlorobenzylamino)benzoic acid. Crystalline substance; m.p. 168° C.

EXAMPLE 14

4-Amino-3-chloro-5-methylbenzoylguanidine dihydrochloride is obtained according to the general procedure from 4-amino-3-chloro-5-methylbenzoic acid. Crystalline substance; m.p. 232°–234° C.

EXAMPLE 15

4-Amino-3,5-dichlorobenzoylguanidine dihydrochloride is obtained according to the general procedure from 4-amino-3,5-dichlorobenzoic acid. Crystalline substance; m.p. 273° C.

EXAMPLE 16

4-Amino-3,5-dichlorobenzoylguanidine dihydrochloride is obtained according to the general procedure from 4-amino-3,5-dichlorobenzoic acid. Crystalline substance; m.p. 273° C.

EXAMPLE 17

3-Chloro-5-ethylaminobenzoylguanidine dihydrochloride is obtained according to the general procedure from 3-chloro-5-ethylaminobenzoic acid. Crystalline substance; m.p. 235° C.

EXAMPLE 18

5-Chloro-2-dimethylaminobenzoylguanidine hydrochloride is obtained according to the general procedure from 5-chloro-2-dimethylaminobenzoic acid. Crystalline substance; m.p. 135° C.

EXAMPLE 19

3-Bromo-4-methyl-5-dimethylaminobenzoylguanidine hydrochloride is obtained according to the general procedure from 3-bromo-4-methyl-5-dimethylaminobenzoic acid. Crystalline substance; m.p. 185° C.

EXAMPLE 20

3-Methylamino-5-trifluoromethylbenzoylguanidine dihydrochloride is obtained according to the general procedure from 3-methylamino-5-trifluoromethylbenzoic acid. Crystalline substance; m.p. 163° C.

EXAMPLE 21

3-Chloro-5-methyl-4-dimethylaminobenzoylguanidine dihydrochloride is obtained according to the general procedure from 3-chloro-5-methyl-4-dimethylaminobenzoic acid. Crystalline substance; m.p. 171° C.

EXAMPLE 22

3,5-Dichloro-4-dimethylaminobenzoylguanidine hydrochloride is obtained according to the general procedure from 3,5-dichloro-4-dimethylaminobenzoic acid. Crystalline substance; m.p. 183° C.

EXAMPLE 23

2-Amino-3-methylbenzoylguanidine hydrochloride is obtained according to the general procedure from 2-amino-3-methylbenzoic acid. Crystalline substance; m.p.>270° C.

EXAMPLE 24

3-Chloro-4-methoxy-5-dimethylaminobenzoylguanidine dihydrochloride is obtained according to the general procedure from 3-chloro-4-methoxy-5-dimethylaminobenzoic acid. Crystalline substance; m.p. 148° C.

EXAMPLE 25

3,5-Dibromo-4-(4-fluorobenzylamino)benzoylguanidine hydrochloride is obtained according to the general procedure from 3,5-dibromo-4-(4-fluorobenzylamino)benzoic acid. Crystalline substance; m.p. 206° C.

We claim:

1. A benzoylguanidine of the formula I

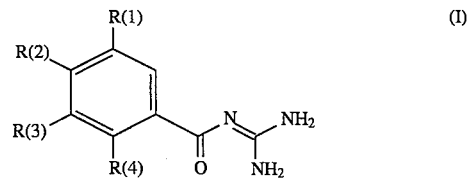

in which: one of the substituents R(1), R(2), R(3) or R(4) is: an amino group

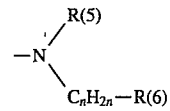

where

R(5)=hydrogen or $C_{(1-6)}$-alkyl, n=zero, 1, 2, 3 or 4,

R(6)=H, $C_{1-4}$-alkyl, in which a $CH_2$ group can be replaced by 1 sulfur atom or a group NR(7) where R(7)=hydrogen, methyl or ethyl, $C_{(3-8)}$-cycloalkyl, phenyl, which is unsubstituted or carries 1, 2 or 3 substituents selected from the group consisting of F, Cl, Br, methyl, methoxy and —NR(8)R(9) where R(8) and R(9) are H, methyl or ethyl, and in which R(5) and R(6), together with the nitrogen atom, can also form a 5-, 6- or 7-membered ring in which 1 carbon atom can be replaced by oxygen, S or NR(10) where R(10) is H, $C_{(1-3)}$-alkyl or benzyl, and the other substituents R(1), R(2), R(3) and R(4) in each case are:

hydrogen, F, Cl, Br, I, CN, $CF_3$, $NO_2$, $CF_3$—O—, $C_mF_{2m+1}$—$CH_2$—O— where m=1, 2 or 3, R(11)—$C_qH_{2q}$—$X_p$— where q=zero, 1, 2, 3 or 4, p=zero or 1,

X=oxygen or NR(12), R(12)=H or $C_{(1-3)}$-alkyl,

R(11)=hydrogen, $C_{1-6}$-alkyl, $C_{(3-8)}$-cycloalkyl, phenyl which is unsubstituted or substituted by 1, 2 or 3 substituents selected from the group consisting of F, Cl, $CH_3$, $CH_3$—O—, NR(13)R(14) where R(13), R(14) is H, methyl or ethyl and where R(1) and R(4) are not simultaneously hydrogen.

2. A compound of the formula I as claimed in claim 1, in which:

one of the substituents R(1), R(2), R(3) or R(4) is: an amino group

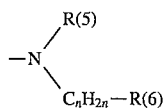

where

R(5)=hydrogen or $C_{(1-4)}$-alkyl, n=zero, 1 or 2, and

R(6)=H, $C_{(1-4)}$-alkyl, in which a $CH_2$ group can be replaced by a sulfur atom or a group NR(7) where R(7)=H, methyl or ethyl, $C_{(3-6)}$-cycloalkyl, phenyl, which is unsubstituted or carries 1, 2 or 3 substituents selected from the group consisting of F, Cl, Br, methyl, methoxy and —NR(8)R(9) where R(8) and R(9) are H, methyl, ethyl, and in which R(5) and R(6), together with the nitrogen atom, can also form a 5-, 6- or 7-membered ring, and the other substituents R(1), R(2), R(3) and R(4) in each case are:

hydrogen, F, Cl, Br, I, $CF_3$, $NO_2$, $C_mF_{2m+1}$—$CH_2$—O— where m=1, 2 or 3, R(11)—$C_qH_{2q}$-$X_p$— where q=zero, 1 or 2, p=zero or 1, X=oxygen R(11)=hydrogen, $C_{(1-6)}$-alkyl, $C_{(5-6)}$-cycloalkyl, phenyl which is unsubstituted or is substituted by 1 or 2 substituents selected from the group consisting of F, Cl, methyl and $CH_2$—O—, and where R(1) and R(4) are not simultaneously hydrogen.

3. A compound of the formula I as claimed in claim 1, in which:

R(4) is hydrogen, one of the substituents R(1), R(2) or R(3) is: an amino group

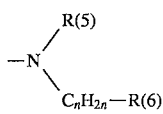

where

R(5)=hydrogen or $C_{(1-4)}$-alkyl, n=zero, 1 or 2, and

R(6)=H, $C_{(1-4)}$-alkyl, $C_{(5-6)}$-cycloalkyl, phenyl, which is unsubstituted or carries 1 or 2 substituents selected from the group consisting of F, Cl and methyl and the other substituents R(1), R(2) and R(3) in each case are:

hydrogen, F, Cl, $CF_3$, R(11)—$C_q$—$H_{2q}$—$X_p$— where q=zero to 2, p=zero or 1, X=oxygen, R(11)=hydrogen, $C_{(1-4)}$-alkyl, $C_{(5-6)}$-cycloalkyl, phenyl which is unsubstituted or substituted by 1 or 2 substituents selected from the group consisting of F, Cl, methyl and $CH_3$—O—, and where R(1) and R(4) are not simultaneously hydrogen.

4. A compound I as claimed in claim 1, selected from the group consisting of 2-amino-3,5-dichlorobenzoyl-guanidine hydrochloride, 5-trifluoromethyl- 3-N,N-dimethylaminobenzoylguanidine hydrochloride, 4-amino-3,5-dibromobenzoylguanidine hydrochloride.

5. A method for the treatment of arrhythmias which comprises administering to a host in need of said treatment an effective amount of a compound of the formula I as claimed in claim 1.

6. A method for the treatment or prophylaxis of cardiac infarct which comprises administering to a host in need of said treatment an effective amount of a compound of the formula I as claimed in claim 1.

7. A method for the treatment or prophylaxis of angina pectoris which comprises administering to a host in need of said treatment an effective amount of a compound of the formula I as claimed in claim 1.

8. A method for the treatment or prophylaxis of ischemic conditions of the heart which comprises administering to a host in need of said treatment an effective amount of a compound of the formula I as claimed in claim 1.

9. A method for the treatment or prophylaxis of ischemic conditions of the peripheral and central nervous system and of stroke which comprises administering to a host in need of said treatment an effective amount of a compound of the formula I as claimed in claim 1.

10. A method for the treatment or prophylaxis of ischemic conditions of peripheral organs and limbs which comprises administering to a host in need of said treatment an effective amount of a compound of the formula I as claimed in claim 1.

11. A method for the treatment of states of shock which comprises administering to a host in need of said treatment an effective amount of a compound of the formula I as claimed in claim 1.

12. A method for protective treatment in surgical operations and organ transplantation which comprises administering to a host in need of said treatment an effective amount of a compound of the formula I as claimed in claim 1.

13. A method for the preservation and storage of transplants for surgical measures which comprises treating said transplants with an effective amount of a compound of the formula I as claimed in claim 1.

14. A method for the treatment of diseases in which cell proliferation is a primary or secondary cause which comprises administering to a host in need of said treatment an effective amount of a compound of the formula I as claimed in claim 1.

15. A method, as claimed in claim 4, wherein the disease is atherosclerosis, late complications of diabetes, a cancer, a fibrotic disease or prostate hyperplasia.

16. A method, as claimed in claim 14, wherein the fibrotic disease is pulmonary fibrosis, fibrosis of the liver or fibrosis of the kidneys.

17. A method for the treatment of diseases caused by gastric acid hypersecretion which comprises administering to a host in need of said treatment an effective amount of a compound of the formula I as claimed in claim 1.

18. A diagnostic agent for the inhibition of the $Na^+/H^+$ exchanger and the diagnosis of hypertension and proliferative disorders which comprises a compound of the formula I as claimed in claim 1.

19. A pharmaceutical composition for the treatment of arrythmias, cardiac infarct, angina pectoris or ischemic conditions of the heart, of the peripheral and central nervous systems, of the peripheral organs and limbs, of stroke and of states of shock which comprises an effective amount for said treatment of a compound of formula I as claimed in claim 1 together with a pharmaceutically acceptable carrier.

* * * * *

UNITED STATES PATENT AND TRADEMARK OFFICE
CERTIFICATE OF CORRECTION

PATENT NO. : 5,516,805
DATED : May 14, 1996
INVENTOR(S) : Hans-Jochen LANG et al.

It is certified that error appears in the above-indentified patent and that said Letters Patent is hereby corrected as shown below:

In the Abstract item [57], line 19, "is chemically" should read --ischemically--.

Claim 1, column 10, line 39, "$C_{(1-6)}$-alkyl," should read --$C_{(1-6)}$-alkyl,--.

Claim 1, column 10, line 41, "$C_{1-4})$-alkyl," should read --$C_{(1-4)}$-alkyl,--

Claim 1, column 10, line 44, "$C_{(3-8)}$-cycloalkyl," should read --$C_{(3-8)}$-cycloalkyl,--.

Claim 1, column 10, line 52, "$C_{(1-3)}$-alkyl" should read --$C_{(1-3)}$-alkyl--.

Claim 1, column 10, line 61, "$C_{(1-3)}$-alkyl" should read --$C_{(1-3)}$-alkyl--.

Claim 1, column 10, line 62, "$C_{1-6})$-alkyl," should read --$C_{(1-6)}$-alkyl, and $C_{(3-8)}$-cycloalkyl," should read --$C_{(3-8)}$-cycloalkyl,--.

UNITED STATES PATENT AND TRADEMARK OFFICE
CERTIFICATE OF CORRECTION

PATENT NO. : 5,516,805
DATED : May 14, 1996
INVENTOR(S) : Hans-Jochen LANG et al.

It is certified that error appears in the above-indentified patent and that said Letters Patent is hereby corrected as shown below:

Claim 2, column 11, line 12, "$C_{(1-4)}$-alkyl," should read --$C_{(1-4)}$-alkyl,--.

Claim 2, column 11, line 14, "$C_{(1-4)}$-alkyl," should read --$C_{(1-4)}$-alkyl,--.

Claim 2, column 11, line 17, "$C_{(3-6)}$-cycloalkyl," should read --$C_{(3-6)}$-cycloalkyl--.

Claim 2, column 11, line 32, "$C_{(1-6)}$-alkyl," should read --$C_{(1-6)}$-alkyl,--, and "$C_{(5-6)}$-cycloalkyl," should read --$C_{(5-6)}$-cycloalkyl,--.

Claim 2, column 11, line 35, "$CH_2$-O-," should read --$CH_3$-O-,--.

Claim 3, column 11, line 50, "$C_{(1-4)}$-alkyl," should read --$C_{(1-4)}$-alkyl,--.

UNITED STATES PATENT AND TRADEMARK OFFICE
CERTIFICATE OF CORRECTION

PATENT NO. : 5,516,805
DATED : May 14, 1996
INVENTOR(S) : Hans-Jochen LANG et al.

It is certified that error appears in the above-indentified patent and that said Letters Patent is hereby corrected as shown below:

Claim 3, column 11, line 51, "$C_{(1-4)}$-alkyl," should read --$C_{(1-4)}$-alkyl,--, and "$C_{(5-6)}$-cycloalkyl," should read --$C_{(5-6)}$-cycloalkyl--.

Claim 3, column 11, line 60, "$C_{(1-4)}$-alkyl," should read --$C_{(1-4)}$-alkyl,--, and "$C_{(5-6)}$-cycloaklyl," should read --$C_{(5-6)}$-cycloalkyl,--.

Signed and Sealed this

Twentieth Day of May, 1997

*Attest:*

BRUCE LEHMAN

*Attesting Officer*     Commissioner of Patents and Trademarks